United States Patent
Wodlinger

(10) Patent No.: US 12,138,107 B2
(45) Date of Patent: Nov. 12, 2024

(54) SYSTEM AND METHOD FOR ULTRASOUND PERFUSION IMAGING

(71) Applicant: Exact Imaging Inc., Ontario (CA)

(72) Inventor: Brian C. Wodlinger, Ontario (CA)

(73) Assignee: EXACT IMAGING INC., Ontario (CA)

(*) Notice: Subject to any disclaimer, the term of this patent is extended or adjusted under 35 U.S.C. 154(b) by 373 days.

(21) Appl. No.: 17/629,008

(22) PCT Filed: Jul. 20, 2020

(86) PCT No.: PCT/CA2020/051002
§ 371 (c)(1),
(2) Date: Jan. 21, 2022

(87) PCT Pub. No.: WO2021/012041
PCT Pub. Date: Jan. 28, 2021

(65) Prior Publication Data
US 2022/0265241 A1    Aug. 25, 2022

Related U.S. Application Data

(60) Provisional application No. 62/878,126, filed on Jul. 24, 2019.

(51) Int. Cl.
*A61B 8/06* (2006.01)
*A61B 8/00* (2006.01)
(Continued)

(52) U.S. Cl.
CPC .............. *A61B 8/06* (2013.01); *A61B 8/461* (2013.01); *A61B 8/5276* (2013.01);
(Continued)

(58) Field of Classification Search
CPC .......................... A61B 8/06; G01S 7/52077
See application file for complete search history.

(56) References Cited

U.S. PATENT DOCUMENTS 8,057,408 B2   11/2011   Cain et al.
9,955,941 B2   5/2018    Rafter et al.
(Continued)

FOREIGN PATENT DOCUMENTS

JP   H08322836 A   12/1996
JP   2001503654 A   3/2001

OTHER PUBLICATIONS

Xiaowei Zhou et al. (2018). 3-D Velocity and vol. Flow Measurement In~Vivo Using Speckle Decorrelation and 2-D High-Frame-Rate Contrast-Enhanced Ultrasound. IEEE Transactions on Ultrasonics, Ferroelectrics, and Frequency Control, 65(12), 2233-2244. https://doi.org/10.1109/TUFFC.2018.2850535 (Year: 2018).*
(Continued)

*Primary Examiner* — Colin T. Sakamoto
*Assistant Examiner* — Tommy T Ly
(74) *Attorney, Agent, or Firm* — Tarolli, Sundheim, Covell & Tummino LLP

(57) ABSTRACT

A perfusion imaging processing method comprising collecting a plurality of digital images comprising sequential B-Mode micro-ultrasound reflectivity data, calculating decorrelation trends of autocorrelated data to determine blood flow and perfusion level, reducing the noise content in the data using the decorrelation trends, and/or forming a visual representation based on the decorrelation trends. The present system and method provides an ultrasonic imaging system and method which provides perfusion data without requiring the use of an injected contrast agent.

17 Claims, 7 Drawing Sheets

(51) Int. Cl.
*A61B 8/08* (2006.01)
*G01S 7/52* (2006.01)
*G01S 15/89* (2006.01)
*G06T 3/40* (2006.01)
*G06T 5/70* (2024.01)
*G06T 7/20* (2017.01)
*G06T 7/32* (2017.01)
*G16H 30/40* (2018.01)
*G16H 50/20* (2018.01)

(52) U.S. Cl.
CPC ........ *G01S 7/52077* (2013.01); *G01S 15/895* (2013.01); *G01S 15/8977* (2013.01); *G06T 3/40* (2013.01); *G06T 5/70* (2024.01); *G06T 7/20* (2013.01); *G06T 7/32* (2017.01); *G16H 30/40* (2018.01); *G16H 50/20* (2018.01); *G06T 2207/10016* (2013.01); *G06T 2207/10132* (2013.01)

(56) References Cited

U.S. PATENT DOCUMENTS

| | | |
|---|---|---|
| 2002/0013530 A1 | 1/2002 | Cespedes et al. |
| 2010/0069797 A1 | 3/2010 | Cain et al. |
| 2015/0320481 A1 | 11/2015 | Cosman et al. |
| 2020/0129154 A1* | 4/2020 | Richardson ............ A61B 8/483 |

OTHER PUBLICATIONS

International Patent Application No. PCT/CA2020/051002; Int'l Written Opinion and Search Report; dated Oct. 5, 2020; 7 pages.

Extended European Search Report (EESR) for corresponding EP Patent Application No. 20844895.1, dated Jul. 18, 2023, 12 pgs.
JP Office Action for corresponding JP Patent Application No. 2022-503852, dated Jan. 9, 2024, 5 pgs.
Chih-Kuang Yeh et al: "The Correlation-Based Algorithm to Perfusion Assessment in Ultrasound Image", Engineering in Medicine and Biology Society, 2005. IEEE EMBS 2005. 27th Annual International Conference of the Shanghai, China Sep. 1-4, 2005, Piscataway, NJ, USA, IEEE, Sep. 1, 2005, pp. 3233-3236, XP010908496, DOI: 10.1109/IEMBS.2005.1617165, ISBN: 978-0-7803-8741-6, abstract; figures 1,2,4,5a-c,6, p. 3234, left-hand column, paragraph 2 p. 3236, right-hand column, paragraph 1.
Rubin J Met Al: "Volume flow measurement using doppler and grey-scale decorrelation", Ultrasound in Medicine and Biology, New York, NY, US, vol. 27, No. 1, Jan. 1, 2001, pp. 101-109, XP004295670, ISSN: 0301-5629, DOI: 10.1016/S0301-5629(00)00291-X, p. 102, right-hand column, paragraph 2, p. 106, right-hand column, paragraph 1; figures 2, 4.
Li W et Al: "Temporal correlation of blood scattering signals from intravascular ultrasound", Ultrasonics Symposium, 1995. Proceedings., 1995 IEEE Seattle, WA, USA Nov. 7-10, 1995, New York, NY, USA, IEEE, US, vol. 2, Nov. 7, 1995, pp. 1515-1518, XP010157396, DOI: 10.1109/ULTSYM. 1995.495842, ISBN: 978-0-7803-2940-9, abstract; figures 4c, 5, p. 1518, left-hand column.
Zhou Xiaowei et al: "3-D Velocity and Volume Flow Measurement $In-Vivo$ Using Speckle Decorrelation and 2-D High-Frame-Rate Contrast-Enhanced Ultrasound", IEEE Transactions on Ultrasonics, Ferroelectrics, and Frequency Control, IEEE, USA, vol. 65, No. 12, Dec. 1, 2018, pp. 2233-2244, XP011701119, ISSN: 0885-3010, DOI: 10.1109/TUFFC.2018.2850535 [retrieved on Dec. 19, 2018], abstract; figures 1, 2, 6, 7,13; table 1.

* cited by examiner

SYSTEM AND METHOD FOR ULTRASOUND PERFUSION IMAGING

CROSS-REFERENCE TO RELATED APPLICATIONS

This application is the National Stage of International Application No. PCT/CA2020/051002 filed Jul. 20, 2020, which claims the benefit of U.S. Provisional Patent Application No. 62/878,126, filed Jul. 24, 2019, the disclosures of which are incorporated herein by reference in their entirety.

FIELD OF THE INVENTION

The present invention pertains to perfusion imaging of tissues in vivo using ultrasound. In particular, the present invention pertains to a method and system for non-invasive perfusion imaging of live tissues using ultrasound and noise reduction of ultrasound images.

BACKGROUND

Dynamic imaging of physiological volume data is used in medicine to detect abnormalities in tissue perfusion, for example to diagnose an acute stroke, brain tumour, or in tumour detection and classification. Ultrasonic imaging or sonography is used to image live tissues in animals and humans. Diagnostic sonography, also referred to as ultrasonography, is an ultrasound-based diagnostic imaging technique used for visualizing subcutaneous body structures of a patient, such as tendons, muscles, joints, vessels and internal organs for possible pathology or lesions. Ultrasound images or sonograms are made by sending a pulse of ultrasound into tissue by using an ultrasound transducer or probe. The sound reflects and echoes off of parts of the tissue, and the echo or reflected sound is recorded and displayed as an image to the operator of a medical-imaging system, usually with denser tissues showing up as bright areas and less dense tissues showing up as darker areas in the sonogram image. The commonest form of ultrasound image is a B-mode image (brightness-mode), which displays the changes in acoustic impedance of a two- or three-dimensional cross-section of tissue.

Doppler ultrasonography is used to study blood flow, including direction and velocity of flow, and muscle motion. The different detected speeds of flow and movement with Doppler images are often represented in color for ease of interpretation. For example, in a leaky heart valve the leak shows up as a flash of unique color. Ultrasound contrast agents comprising encapsulated gaseous microbubbles can be used to increase echogenicity in tissues, or improved ability to echo sound waves. The contrast medium is intravenously administered to introduce the gas-filled microbubble contrast agent to the systemic circulation, and the increased echogenicity provides an enhanced image used to image blood perfusion in organs. Perfusion imaging provides information about physiological tissue behaviour such as blood volume, blood flow, mean transit time (MTT) and time to peak (TTP) in vascularized tissue. Without contrast media, blood flow in tissues is challenging or impossible to detect unless the blood vessels are above a certain minimum size, such as in the heart, are oriented favorably to the imaging plane, and have a reasonably high flow rate although this minimum flow rate and vessel size are slightly lower for power doppler than color doppler.

Unlike color flow imaging modes which measure flow, it is desirable to measure the perfusion level within biological tissues.

In perfusion imaging typically a bolus of a contrast agent is injected and its distribution is followed by a repeated acquisition of subsequent images covering the volume of interest. The contrast agent works as a tracer of the blood and provides signal changes to indicate blood flow. Depending on the actual physiological process, either the short-term distribution (<1 min) of blood flow (perfusion) or the long-term (>1 min) diffusion process of the tracer particles through the membranes of the micro-vessels (tissue kinetics) are encoded in the varying signal of the image voxels. The extracted time-intensity curves for each voxel are typically converted into relative concentration-time curves. Conventional ultrasound resolution limits the minimum side-length of the voxel to >150 microns.

High frequency ultrasound, also known as micro-ultrasound, is becoming a valuable diagnostic technique due to the development of high-frequency ultrasound array transducers. In micro-ultrasound systems, sound waves in the range of 15 to 80 MHz are generated from transducers and then propagated through living tissues which reflect these sound waves which then come back to the transducer. The sound waves are then translated into two- and three-dimensional images. A benefit of high frequency ultrasound is the ability to image small voxel size, which improves the resolution of the image.

In one example of ultrasound imaging, U.S. Pat. No. 9,955,941 to Rafter et al. describes an ultrasonic diagnostic imaging system which scans a plurality of planar slices in a volumetric region containing tissue which has been perfused by a contrast agent. Following detection of the image data the slice data is combined by projecting the data in the elevation dimension to produce an elevationally combined slice image and the image data is combined by means of an averaging or maximum intensity detection or weighting process or by raycasting in the elevation dimension in a volumetric rendering process. The combined slice image provides a measure of perfusion.

There remains a need for an ultrasonic imaging system and method which provides perfusion data without requiring a contrast agent.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an ultrasonic imaging system and method which provides perfusion data without requiring a contrast agent.

In an aspect there is provided an imaging processing method comprising, processing a plurality of digital images comprising sequential B-Mode ultrasound reflectivity data, calculating decorrelation trends of autocorrelated data to determine flow and perfusion level.

In an embodiment, the method reduces noise content in the ultrasound data using the decorrelation trends. In another embodiment, the method forms a visual representation of the perfusion level based on the decorrelation trends. In another embodiment, the method reduces noise content in the autocorrelated data using the decorrelation trends; and forms a visual representation of the perfusion level based on the decorrelation trends. In another embodiment, the method has an image capture rate of 20 frames/sec or higher. In another embodiment of the method, the image data is standardized before autocorrelation. In another embodiment of the method, the autocorrelated data is normalized. In another embodiment of the method, the decorrelation trend of the autocorrelated data is determined by linear regression, average difference, or overall magnitude change. In another embodiment of the method, the autocorrelated data with non-linear trends are processed to determine one or more of period, exponential decay rate, time to local minima, or another measure of decorrelation. In another embodiment, the autocorrelation is calculated using a Spearman correlation, Pearson correlation, or Fourier Transform. In another embodiment, the method further comprises a smoothing step prior to visual representation of the signal. In another embodiment, the method further comprises application of thresholds and rescaling to the decorrelation trends before visual representation. In another embodiment, the method further comprises a logarithmic transformation of the decorrelation trend. In another embodiment of the method, the decorrelation trends are mapped to different colour or grayscale values for representation in an image. In another embodiment, the method further comprises comprising alignment of the plurality of digital images to correct for movement by matching local signal patterns between frames. In another embodiment, the method includes at least 5 frames of sequential B-Mode ultrasound reflectivity data. In another embodiment of the method, a subset of the image field is processed from each image to decrease processing time. In another embodiment of the method, the image is downsampled to a lower resolution to decrease processing time. In another embodiment of the method, the ultrasound data is high frequency ultrasound with a frequency range greater than 15 MegaHertz.

Another aspect is to provide, a perfusion imaging system comprising, a high frequency ultrasound transducer for capturing and/or collecting a plurality of digital images comprising sequential B-Mode ultrasound reflectivity data, a signal processing unit, operatively connected to the transducer, the signal processing unit configured to calculate decorrelation trends of autocorrelated data to determine blood flow and perfusion level.

Another aspect is to provide, a computer readable storage medium, comprising executable instructions that when executed by a process cause the processor to, process a plurality of digital images comprising sequential B-Mode ultrasound reflectivity data obtained using a micro-ultrasound, calculate decorrelation trends of autocorrelated data to determine blood flow and perfusion level.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION OF THE INVENTION

Figure 1:
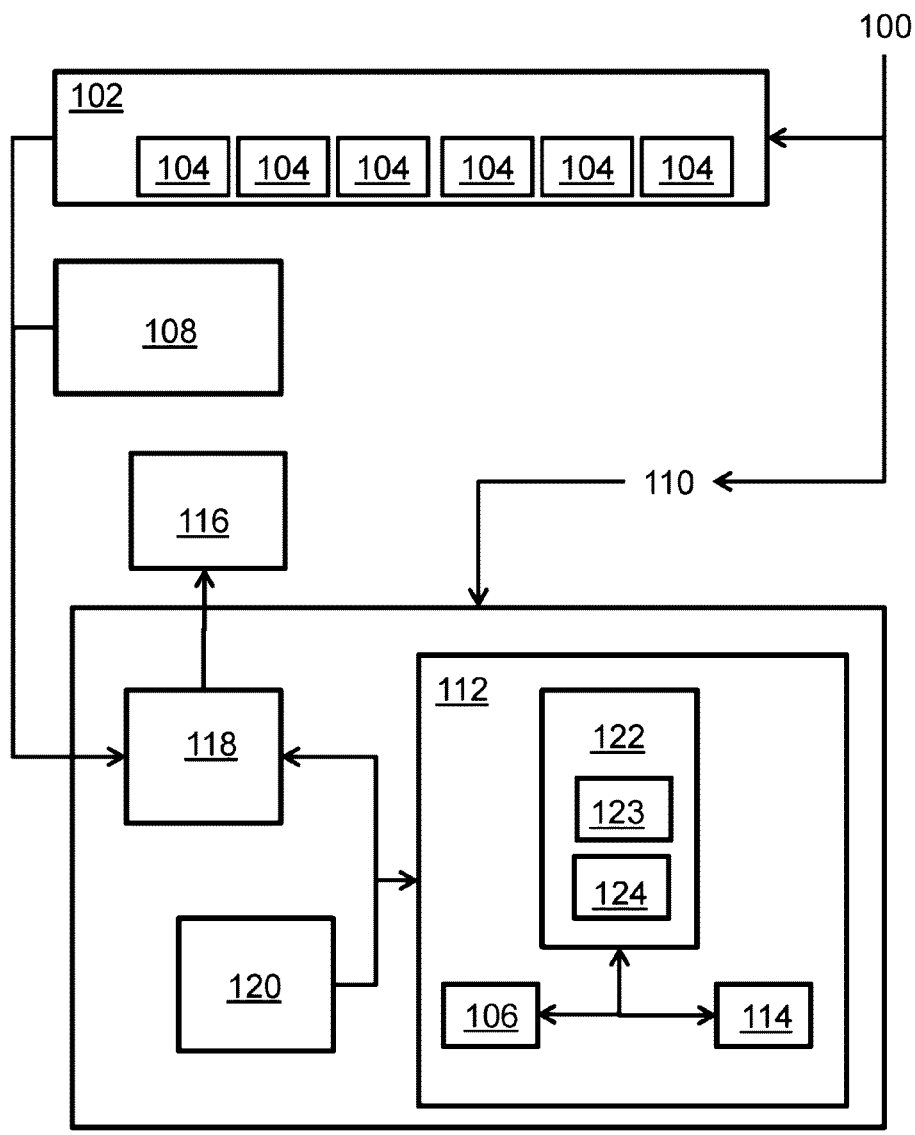
FIG. 1 illustrates a high frequency medical-imaging system.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

Herein is provided an ultrasound mode for perfusion imaging of tissues. In particular, the present system and method provides an ultrasonic imaging system and method which provides perfusion data without requiring the use of an injected contrast agent. By leveraging certain functions of the autocorrelation sequence in the collected ultrasound images, perfusion of blood can be detected and differentiated from what would otherwise be noise in the ultrasound signal. In this way, perfusion within biological tissues can be measured without the need for a contrast agent.

The detection and imaging of the perfusion of blood through tissues can be done by examining the time-decorrelation signal at the pixel level of a micro-ultrasound image configured to a very high frame rate. For example, use in a technique such as plane wave imaging. At the high frame rate and small voxel size provided by micro-ultrasound, the movement of individual reflectors into and out of the sensitive detectable area cause slow changes over time. The detection of these changes over time as a result of blood perfusion through the tissue contrasts with both noise, which is entirely uncorrelated over time, and solid tissue which is correlated over time. Measurement of perfusion in this way may be more difficult in conventional ultrasound because the sensitive area (voxel) in the tissue is too large and too many reflectors pass in and out at once causing the intensity variation to be small due to averaging. Further, conventional ultrasound is not sensitive to the individual reflectors in the blood, while higher frequency micro-ultrasound is. In another embodiment, it is predicted that measurement of perfusion using conventional ultrasound may be possible with the use of another reflector. For example, a large protein or a macrophage may function as a reflector for convention ultrasound.

Without being bound by theory, it is hypothesized that cells in the blood stream serve as an endogenous contrast agent and can be detected with the appropriate signal processing as presently described. In particular, red blood cells (erythrocytes) are the most abundant cell in the blood accounting for about 40 to 45 percent of its volume. Red blood cells have a diameter of approximately 6-8 μm, which is in the same size range as ultrasound microbubble contrast agents, and can have sufficient echogenicity that can be detected by micro-ultrasound. Capillary blood flow rates are on the order of less than a millimetre/second, or around 0.03 cm/s, and perfusion at these rates can be detected using high frequency micro-ultrasound with the presently described imaging mode. This is compared to faster arterial flow of tens of mm per second which is capable of being imaged using conventional low frequency ultrasound such as echocardiography. Capillaries are about 5-10 microns (μm) in diameter, so small that red blood cells can generally only travel through them in single file. The average density of capillaries in human tissue is ~600/mm³ which implies a mean separation of ~40 microns between adjacent capillaries. There are limitations for using contrast agents, such as, requiring an injection, may not be approved for use in all jurisdictions, may not be approved for all uses, and contrast agents may burst or dissipate over time. Contrast agents may work in ultrasound because they are filled with gas and due to the way they oscillate and produce a non-linear response.

If the frame rate for image collection is not fast enough, then the time between frames becomes too large and results in too many reflectors moving in and out of the voxel simultaneously. In this case, an averaging occurs that obscures the correlation of signals. Accordingly, the frame rate must be at least as fast as reflector movement to ensure that blood perfusion through the tissue can be captured. In an embodiment, the frame rate is approximately at least a frame rate of greater than or equal to ($\geq$=) 30 s$^{-1}$. In another embodiment, the frame rate is approximately at least a frame rate of greater than or equal to ($>$) 20 s$^{-1}$ and motion compensation is also required.

In addition, the voxel or sensitive area size imaged in the tissue must be small enough to observe and detect individual or some number of reflectors (i.e. so that some portion of reflectors are present in the same voxel across frames) as they perfuse through the voxel. In an embodiment, the voxel size is on the order of 70 μm. The voxel size of about 70 μm corresponds to a high frequency ultrasound of greater than or equal to ($\geq$=) 15 MHz. A skilled person understands that voxel size varies with the frequency of the ultrasound.

Increased blood flow in a tissue can occur during exercise, and an increase in vascularization brought on by angiogenesis is characteristic of many cancers and tumours. Under conventional ultrasound blood looks dark, and with high frequency ultrasound in the absence of signal decorrelation blood looks like noise. It has been found that increased capillary vascularization can be visualized by changing the micro-ultrasound imaging settings so that images are collected fast enough to monitor changes in the ultrasound signal by limiting the number of scan lines and focal zones and isolating the decorrelated signal characteristic of capillary blood flow. In particular, it has been found that by observing how the noise in high frequency ultrasound changes over time in a particular location, the signal coming from vascularized tissue previously observed as noise can be identified as echo-reflective blood. The present technique is thus able to identify and image areas of perfusion inside tissues.

Unlike in Doppler ultrasound where the blood vessel or capillary needs to flow directly across the imaging plane to see blood flow movement, the detection of echogenicity in each measured voxel in the tissue imaged using the presently described high frequency ultrasound method is agnostic with regard to capillary orientation. By using only the magnitude information in each voxel and no phase or spatial information the present imaging mode is entirely agnostic in regard to direction of flow. That means if there are a bundle of capillaries in the same voxel, with each capillary flowing in different and/or opposite directions, the present imaging mode would still be able determine the total flow rate over all of them. With conventional Doppler ultrasound even if you had two vessels in the same voxel aligned with the imaging plane, if they were flowing in opposite directions one would not see any signal because they would cancel out.

In B-mode (brightness mode) ultrasound, also referred to as 2D mode, a linear array of transducers simultaneously scans a plane through the body that can be viewed as a two-dimensional image on screen. B-mode is an ultrasound imaging mode that digitally highlights moving reflectors, likely to be mainly red blood cells, while suppressing the signals from the surrounding stationary tissue. B-mode can thus visualize flowing blood and surrounding stationary tissues simultaneously. Each pixel in the B-mode image represents a volume of tissue 70 μm in breadth. A typical capillary has a diameter of less than 70 μm, so the image collected is aggregated over capillaries within a tissue volume, which provides a brightness correlated with increased capillary flow to the perfused region.

Data of the resolution provided by micro-ultrasound in B-mode produces a perfusion image that is approximately 5 megapixels/image, with areas of increased blood perfusion showing up as areas of brightness in the image. Using B-Mode, images are collected at a high frame rate (at least 20 frames per second) for a quantity of frames sufficient for comparison and data autocorrelation, for example at least 5 frames.

Image processing of the micro-ultrasound data uses the time constant of brightness variation in each pixel and looks at the rate of statistical change between time points and over time. Optionally, the image may be processed to decrease processing time, for example by selecting a subset of pixels or through the creation of a lower resolution downsampled version of the image. The image may also be optionally processed spatially or temporally to reject noise, smooth the image, and improve fidelity. For example, in an embodiment, a low pass or a filter may be applied first to the image.

The signal is the slope of correlation trend, which is the decorrelation rate. The slope of the decorrelation provides information about how quickly fluid in the perfused area is flowing.

To derive the signal from the images, the data in each pixel is first statistically standardized across all the frames, using the equation:

$$x_{norm} = \frac{x - \text{mean}(x)}{std(x)}$$

Autocorrelation is then calculated to look at repetition of the standardized signal at each pixel, using $x_{norm}$ as the basis for the correlation. Autocorrelation looks at the similarity between the signal at the pixel and the signal at the same pixel after period of time, for example 1 to 4 frames later (0.03 to 0.13 seconds at 30 frames per second.)

Autocorrelation y can be calculated from the standardized image data using the equation:

$$y_{i,j,lag} = \sum_t x_{i,j,t} \cdot x_{i,j,t+lag}$$

where:
i and j represent the 2D coordinates of a pixel,
t is the time index of one image frame being processed, and
lag is the amount of time between that frame and another frame measured in number of frames.

The results of the autocorrelation can be normalized using the equation:

$$y_{i,j,lag,norm} = \frac{y_{i,j,lag}}{N - lag - 1}$$

where:
n is the number of time points (i.e. frames) collected for analysis.

Some other methods that may be used to calculate autocorrelation of the data include Spearman correlation, Pearson correlation, or Fourier Transform. Optionally, the calculated autocorrelation can be smoothed, for example using a gaussian kernel function.

The decorrelation rate is the trend in the normalized autocorrelation of the standardized B-Mode signal over time. The decorrelation rate may be used to measure tissue perfusion, including rates of flow, and to differentiate between tissue types. Typically, time scales can be chosen where signal changes linearly over time, and therefore the decorrelation rate can be determined quantitatively by applying linear regression to fit to a straight line, average difference (by taking the mean of the difference between each point at t and t+1), or the overall magnitude change (max(y)−min(y)). Other calculations could be applied to fit more complex data and give other information about flow, and may include determination of period, exponential decay rate, or time to local minima.

Voxels with very low or negligible decorrelation rates represent noise since noise is an uncorrelated process. Thus, in one embodiment voxels with decorrelation rate below a specified threshold (chosen empirically based on noise level) are set to 0 in the B-Mode image before display, reducing the noise content of the image, improving the signal to noise ratio and contrast. In another embodiment, brightness of pixels in the B-Mode image is reduced based on the decorrelation rate when this rate is below a certain threshold as shown in the following equation. One skilled in the art will understand that the parameters are set empirically to optimize image quality for a specific situation and other similar functions may be employed to the same effect.

$$Brightness_{Out} = Brightness_{In} \cdot \begin{cases} 1 & rate > threshold \\ rate \cdot A & rate \leq threshold \end{cases}$$

It is useful to create a visual representation of the decorrelation rate, which represents aspects of perfusion. In one simple mapping, decorrelation values are assigned a brightness (0-255) which can be displayed on the screen as an image. A threshold may be useful below which the values are not used (e.g. slopes <10=brightness value 0). A logarithmic mapping may also be used to "compress" the signal similar to the compression performed on ultrasound B-Mode imaging data where brightness=log(slope+1) in order to show less difference between the higher values and accentuate differences in the lower values. Other transformations of the data may also be applied as determined to be useful to highlight aspects of interest, which may include flow rate. In some representations, different colours may be used to further discriminate between aspects of interest.

In an embodiment, the perfusion imaging and the noise reduction are based on the decorrelation rate of the voxels. The perfusion imaging and noise reduction may be applied independently of each other. Or, the perfusion imaging and noise reduction may be used together.

Ultrasound systems which can be used to collect the data for the present imaging method should be those adapted to receive ultrasound signals having a frequency of at least 15 megahertz (MHz) with a frame rate of at least 20 frames per second (fps). Compared with conventional ultrasound imaging which typically use frequencies from 2 to 15 MHz, high frequency (HF) imaging (higher than 15 MHz) yields improved spatial resolution. The signal processing as presently described requires a higher frame rate to produce an ultrasound image from the acquired ultrasound signal. In another embodiment, the signal processing may work with conventional ultrasound frequencies with strong reflectors, such as microbubble contrast agents and/or nanoparticle contrast agents.

The transducer used for image collection can be a linear array transducer, a phased array transducer, a two-dimensional (2-D) array transducer, or a curved array transducer. The center transmit frequency of the transducer used is preferably equal to or greater than 15 MHz. For example, the center transmit frequency can be approximately 15 MHz, 20 MHz, 30 MHz, 40 MHz, 50 MHz, 55 MHz or higher. In some exemplary aspects, the ultrasound transducer can transmit ultrasound into the subject at a center frequency within the range of about 15 MHz to about 80 MHz. Preferably the transducer comprises a high frequency linear array, with an imaging system in the 20-50 MHz range.

FIG. 1 shows a high frequency medical-imaging system 100 for use with the present methods includes an ultrasound transducer 102 having transducer elements 104, an ultrasound-transducer interface 106, a spatial sensor 108, and a server 110. The ultrasound transducer 102 is configured to: (A) convert the echo sound signal that was received (by the ultrasound transducer 102) into ultrasound information; and (B) transmit the ultrasound information (via an output port). The ultrasound transducer 102 is also called an ultrasound probe. The ultrasound transducer 102 has the transducer elements 104 arranged in an array; for example, the transducer elements 104 may be aligned along a row, relative to each other, one after the other. The transducer elements 104 are configured to be activated (they may be selectively activated or not activated). The transducer elements 104 are also called transmit and receive elements, in that they transmit ultrasound pulses and receive reflections of the ultrasound pulses. A collection of the transducer elements 104 is also called the transducer array. The ultrasound transducer 102 is also known as an ultrasonic transceiver for the case where the ultrasound transducer 102 is configured to both send (an outgoing ultrasonic pulse) and receive (a reflected ultrasonic pulse). The medical-imaging system 100 uses the ultrasound transducer 102 on a principle similar to radar or sonar, in which the medical-imaging system 100 is configured to evaluate attributes of a target by interpreting the echoes (reflections) from sound waves. The ultrasound transducer 102 is configured to: (A) generate relatively higher frequency sound waves; and (B) receive the echo from the target. The medical-imaging system 100 is configured to: (A) evaluate the ultrasound information provided by the ultrasound transducer 102; (B) calculate the time interval between sending the outgoing signal (from the ultrasound transducer 102) and receiving the echo; (C) determine the distance to the target or an object based on the time interval that was calculated. The ultrasound transducer 102 is configured to generate sound waves in the ultrasonic range, above about generally 18 KHz (Kilo Hertz), by turning electrical energy into sound; then, upon receiving the echo, the ultrasound transducer 102 is configured to turn the reflected sound waves into electrical energy, which can be measured and displayed by the medical-imaging system 100.

Ultrasound is an oscillating sound pressure wave with a frequency greater than the upper limit of the human hearing range. Although this limit varies from person to person, it is approximately 20 KHz in healthy, young adults. Some ultrasound devices operate with frequencies from about 20 kHz up to several gigahertz (GHz). The ultrasound transducer 102 is configured to transmit a signal that includes short bursts of ultrasonic energy. After each burst, the ultrasound transducer 102 is configured to receive a return (reflected) signal within a small window of time corresponding to the time taken for the energy to pass through the tissue of the patient; the signals received during this period then qualify for additional signal processing by the medical-imaging system 100. The ultrasound transducer 102 (medical ultrasonic transducer or probe) may be configured to have any variety of different shapes and sizes for use in making pictures of different parts of the body. The ultrasound transducer 102 may be passed over the surface of the body (patient), inserted laparoscopically, or into an orifice (body opening) of the patient, such as the esophagus, rectum, or vagina. The ultrasound transducer 102 may be configured (by clinicians or operators who perform ultrasound-guided procedures) for use with a probe-positioning system (not depicted and known) configured to hold and/or move the ultrasound transducer 102; the ultrasound transducer 102 includes an array of the transducer elements 104. The row of the transducer elements 104 of the ultrasound transducer 102 may be aligned in a rectilinear arrangement, or in a curvilinear arrangement. Each of the transducer elements 104 are configured to: (A) transmit an incident sound signal toward a target; and (B) receive an echo sound signal representing sound being reflected back from the target to the transducer elements 104.

The ultrasound-transducer interface 106 is configured to control operation of the ultrasound transducer 102. The ultrasound-transducer interface 106 is depicted in FIG. 1 as a software program (in accordance with an option). The processor assembly 120 controls the ultrasound transducer 102 via the ultrasound-transducer interface 106. The ultrasound-transducer interface 106 is also called a beam-former. In accordance with an example, the ultrasound-transducer interface 106 may include server-executable code (a software program) tangibly stored in a non-transitory computer-readable medium 112 (hereafter referred to as the memory 112) of the server 110; in accordance with another example, the ultrasound-transducer interface 106 includes a combination of electronic hardware components that cooperate with server-executable code. In general terms, the ultrasound-transducer interface 106 is configured to: (A) operatively connect to the ultrasound transducer 102 (via the output port of the ultrasound transducer 102); (B) control the shape of the incident sound signal to be transmitted by the transducer elements 104; (C) receive the ultrasound information from the ultrasound transducer 102; and (D) provide the scan lines that are mapped to the transducer elements 104 that are activated in such a way as to generate the scan lines to be provided (not all of the transducer elements 104 will be activated and thus these unused instances of the transducer elements 104 will be inactivated). The ultrasound-transducer interface 106 is a device configured to facilitate electronic controlled focusing of the ultrasound energy emitted and/or received by the ultrasound transducer 102.

Generally, the spatial sensor 108 is configured to: (A) detect spatial movement of the ultrasound transducer 102; and (B) provide spatial information indicating spatial movement of the ultrasound transducer 102 while the ultrasound transducer 102 transmits ultrasound information to the ultrasound-transducer interface 106. The spatial sensor 108 may be attached to the ultrasound transducer 102. Alternatively, the spatial sensor 108 may be integrated with the ultrasound transducer 102.

The server 110 is also known as a computer, etc. Generally, the server 110 is configured to: (A) interface with the ultrasound-transducer interface 106; (B) interface with the spatial sensor 108; and (C) have a memory 112 tangibly storing the executable code 114 (also called processor-executable code, and hereafter referred to as the program 114). The program 114 is a combination of operational tasks to be executed by the server 110. The server 110 is a system that is a combination of software and suitable computer hardware. The server 110 may include a dedicated computer or a combination of computers. The server 110 may be configured for client-server architecture (if so desired).

The memory 112 may refer to the physical devices used to store computer executable programs or processor executable programs (sequences of instructions or operations) and/or data (e.g. program state information) on a temporary basis or a permanent basis for use in the server 110 and anything equivalent thereof. Primary memory is used for the information in physical systems which function at high-speed (such as, RAM or Random Access Memory), as a distinction from secondary memory, which are physical devices for program and data storage which are slow to access but offer higher memory capacity. Primary memory stored on secondary memory is called "virtual memory". By way of example, the memory 112 may include volatile memory and/or non-volatile memory. By way of example, the memory 112 may include secondary memory such as tape, magnetic disks and optical discs (CD-ROM or Compact Disc ROM, and DVD-ROM or Digital Video Disc ROM), etc.

The program 114 is constructed using known software tools as known to those skilled in the art; computer programmed instructions are assembled, in a high level computer programming language, and a compiler and other tools are used to convert the computer programmed instructions into the executable code. It will be appreciated that the program 114 provides a method or a sequence of operations to be executed by the processor assembly 120. The memory 112 includes (tangibly stores) the executable code 114 (also called the program 114). The executable code 114 includes a combination of operational tasks to be executed by the processor assembly 120. For instance, the executable code 114 is configured to direct the server 110 to receive ultrasound information associated with a scan-line set having a limited number of selectable scan lines of the ultrasound transducer 102. By way of example (and not limited thereto), the scan-line set may have a limited number of scan lines that are mapped with a limited set of the transducer elements 104 of the ultrasound transducer 102 (that were used to generate the selected scan lines of the scan-line set), if so desired.

It will be appreciated that in view of the above, there is provided, in general terms, a method of operating the medical-imaging system 100 having the ultrasound-transducer interface 106; the ultrasound-transducer interface 106 is configured to operatively interface with the ultrasound transducer 102; the ultrasound transducer 102 includes transducer elements 104; the medical-imaging system 100 also has the spatial sensor 108 configured to provide spatial information indicating spatial movement of the ultrasound transducer 102; the method includes receiving ultrasound information associated with the scan-line set having the limited number of selectable scan lines of the ultrasound transducer 102. In addition, the server 110 is configured (programmed) to receive ultrasound information associated with a scan-line set having a limited number of selectable scan lines of the ultrasound transducer 102. In addition, the non-transitory computer-readable medium 112 includes executable code 114 that is tangibly stored in the non-transitory computer-readable medium 112; the executable code 114 includes a combination of operational tasks that are executable by the server 110); the executable code 114 is configured (programmed) to direct the server 110 to receive ultrasound information associated with the scan-line set having the limited number of selectable scan lines of the ultrasound transducer 102.

The server 110 also includes a display assembly 116; an input/output interface module 118; a processor assembly 120; a database 122 tangibly stored in the memory 112; ultrasound data 123; and spatial data 124. The ultrasound data 123 and the spatial data 124 are stored in the database 122 or are stored in the memory 112. The input/output interface module 118 is configured to operatively connect the processor assembly 120 with the display assembly 116, the ultrasound-transducer interface 106 (and indirectly, the ultrasound transducer 102) and the spatial sensor 108. In this manner, the processor assembly 120 may control operations of the display assembly 116, the ultrasound-transducer interface 106, and the spatial sensor 108, and also control the ultrasound transducer 102 via direct control of the ultrasound-transducer interface 106. The input/output interface module 118 is also configured to interface the processor assembly 120 with user-interface devices (such as a keyboard, a mouse, a touch-screen display assembly, etc.).

The processor assembly 120 (also called a central processing unit or CPU or a central processor unit) is the hardware within the server 110 that carries out the instructions as set out in the program 114 by performing the arithmetical, logical, and input/output operations. The processor assembly 120 may have one or more instances of the CPU. The CPU may include a microprocessor (meaning the CPU is contained on a single silicon chip). Some integrated circuits (ICs) may contain multiple CPUs on a single chip; those ICs are called multi-core processors. An IC containing a CPU may also contain peripheral devices, and other components of a computer system; this is called a system on a chip (SoC). Components of the CPU are the arithmetic logic unit (ALU), which performs arithmetic and logical operations, and the control unit (CU), which extracts instructions from memory and decodes and executes them, calling on the ALU when necessary. The processor assembly 120 may include an array processor or a vector processor that has multiple parallel computing elements, with no one unit considered the "center". In the distributed computing model, problems are solved by a distributed interconnected set of processors. The images to be displayed by a medical-imaging system 100 may be displayed in real-time and/or after an acquisition or processing delay (via the display assembly 116).

Figure 2A:
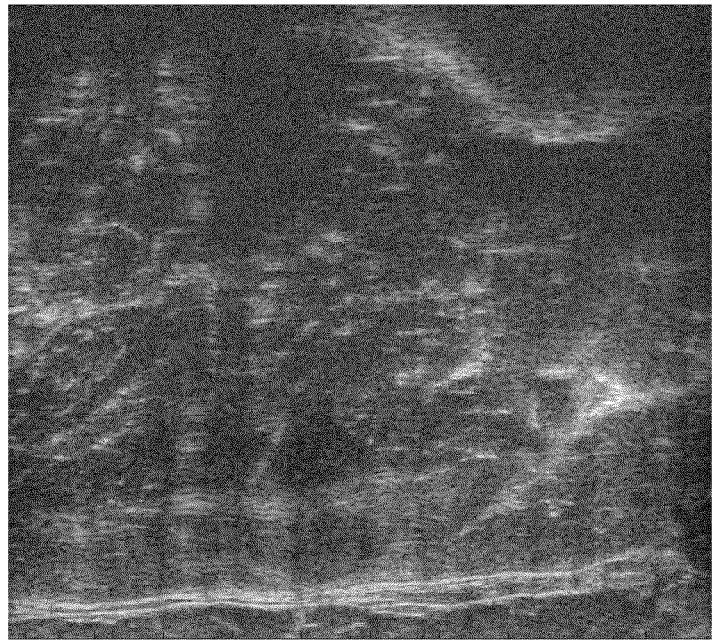
FIGS. 2A and 2B are example ultrasound images before and after denoising by eliminating low-correlation pixels.
Figure 2B:
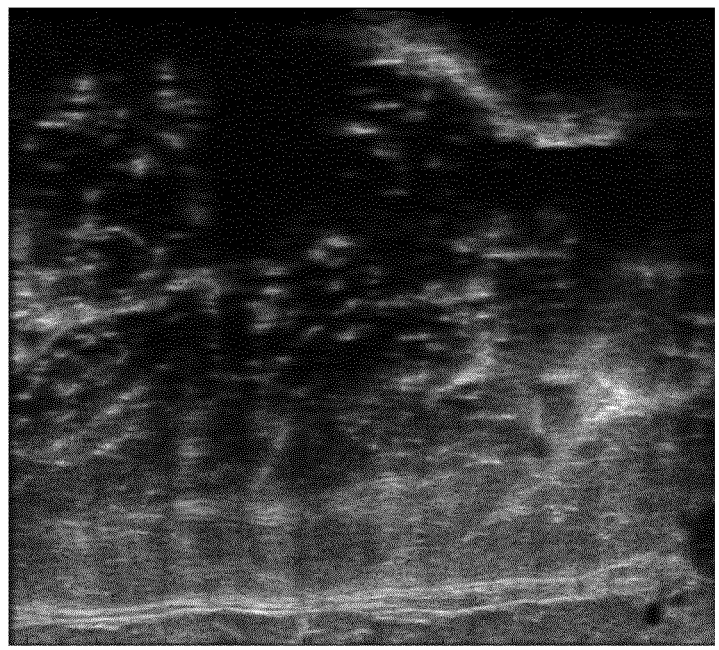

FIGS. 2A and 2B are ultrasound images before and after denoising by eliminating pixels with very short decorrelation times. These pixels are typically a product of random noise in the received signal rather than true biological effects, as distinct from pixels with measurable medium or long decorrelation times which are related to flow or static anatomical structures. By removing or reducing amplification on these short decorrelation pixels the overall signal-to-noise ratio of the image is improved. FIG. 2A shows an image before correction. While FIG. 2B shows the same image with the short decorrelation time pixels removed (after correction).

In addition to brightening the perfusion area to highlight areas of blood flow, the brightness signals of areas of the surrounding stationary tissue can be suppressed to provide contrast between perfused and non-perfused tissue.

Figure 3:
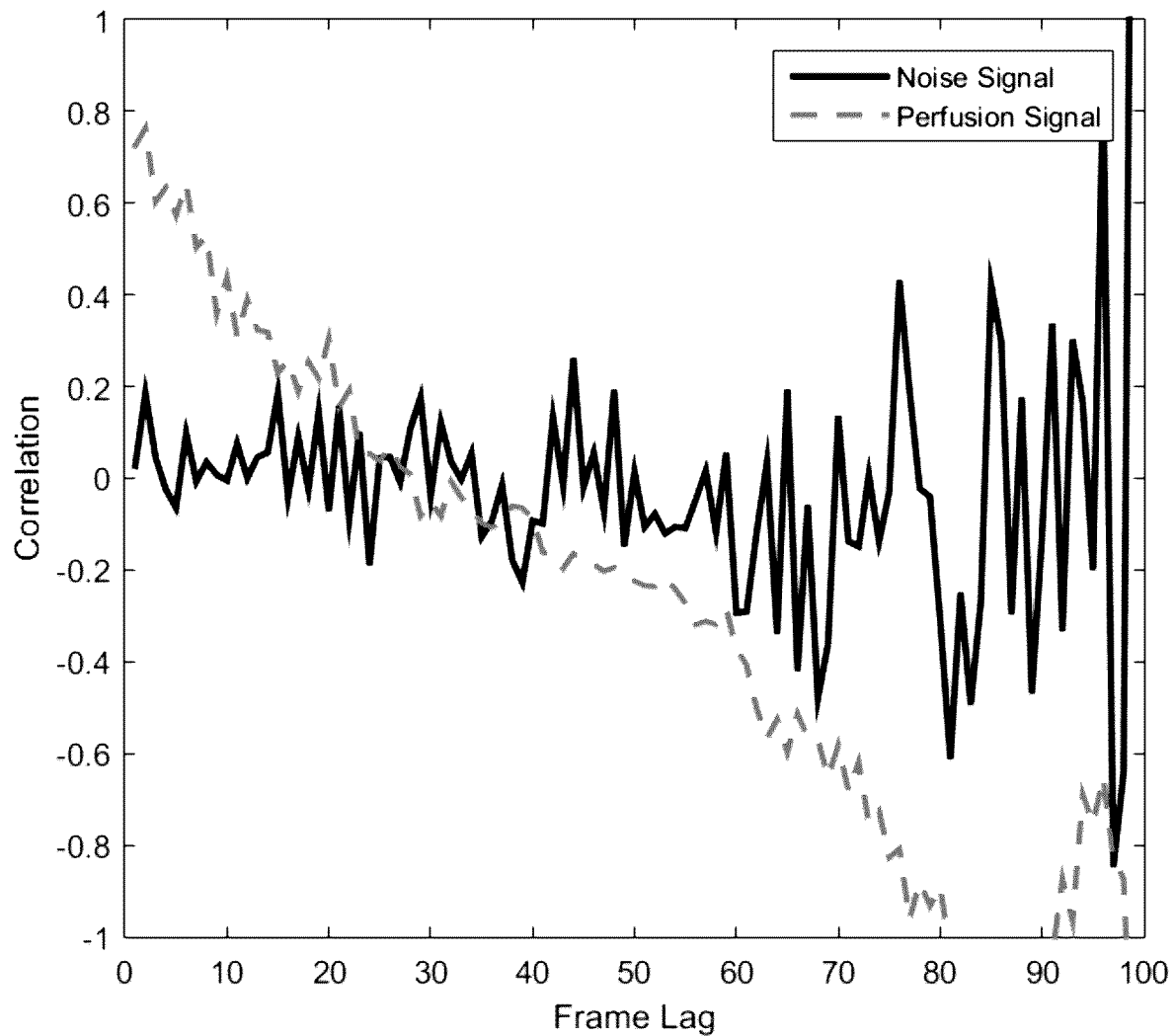
FIG. 3 shows an example of a perfusion signal from a blood vessel as compared to an area of noise in the image.

FIG. 3 shows an example of a perfusion signal from a blood vessel as compared to an area of noise in the image. The blood signal has a clear linear slope. While the noise signal appears random, with no overall trend.

Figure 4:
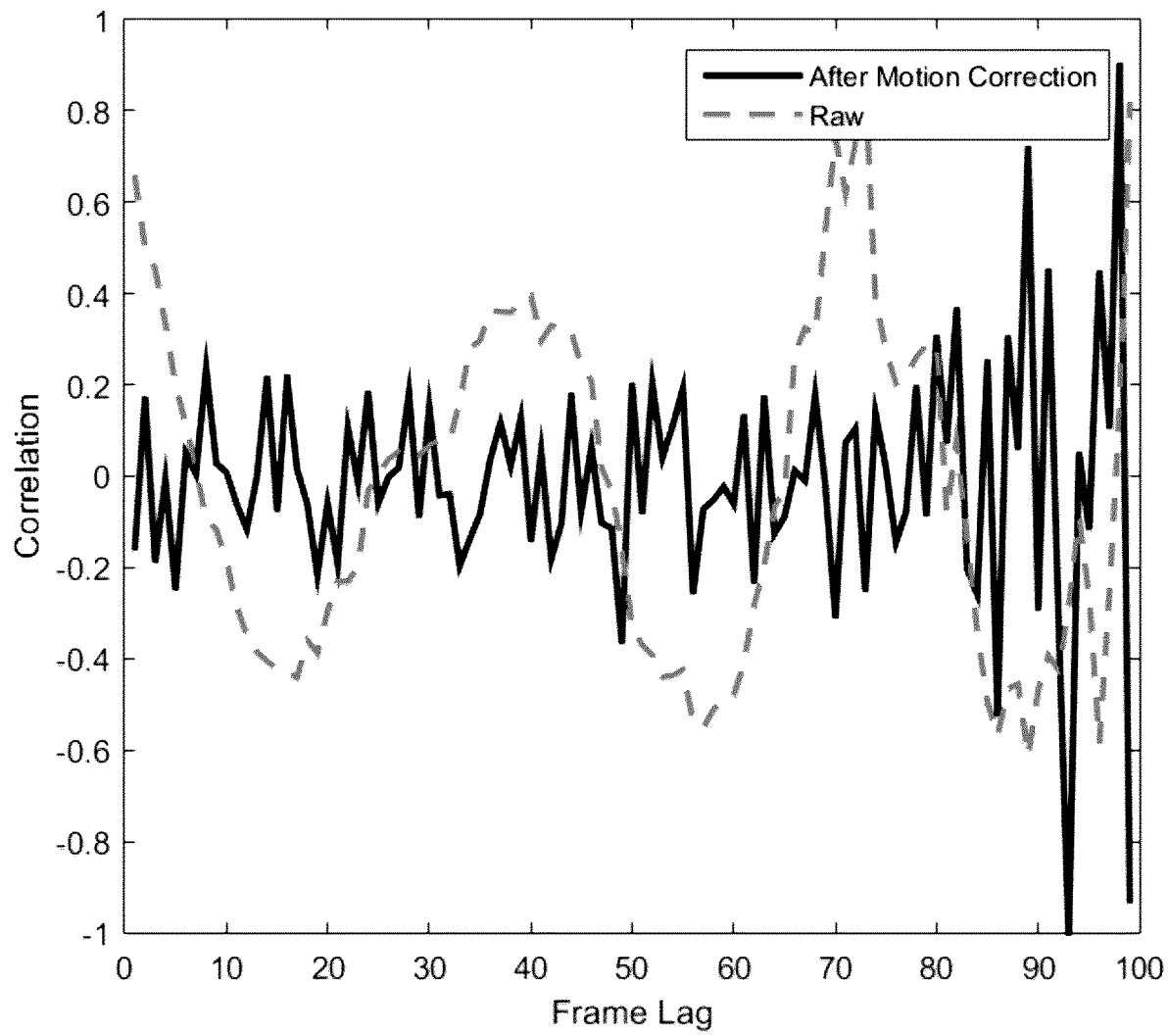
FIG. 4 shows an example of the signal from unaligned and aligned images.

FIG. 4 shows an example of the signal from unaligned and aligned images with the aberrant signal from movement during imaging removed. Movement of or within the target area may also occur during image collection. For example, this may occur due to the patient moving, or movements of tissues and organs in the body. Optionally, images may be aligned to correct for this movement by matching local signal patterns between frames. In one alignment method, the neighbourhood of each pixel is identified and the time-dependent cross-correlation of signal across the 2D grid of pixel neighbourhoods is matched to remove aberrant signals. Faster imaging rates may be useful to reduce alignment issues.

Figure 5A:
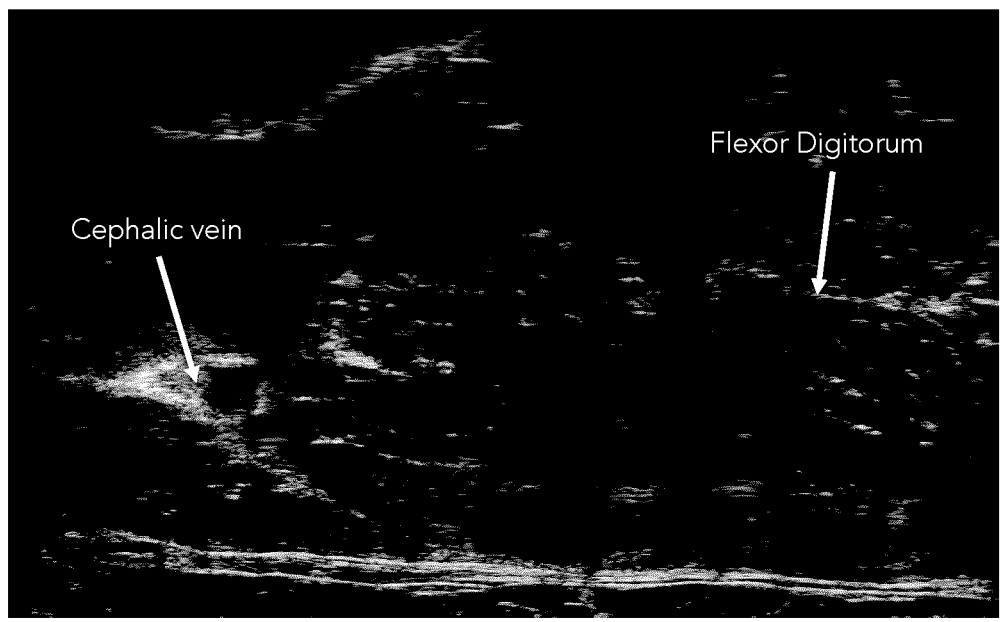
FIGS. 5A-C are examples before and after activation of a forearm muscle.
Figure 5B:
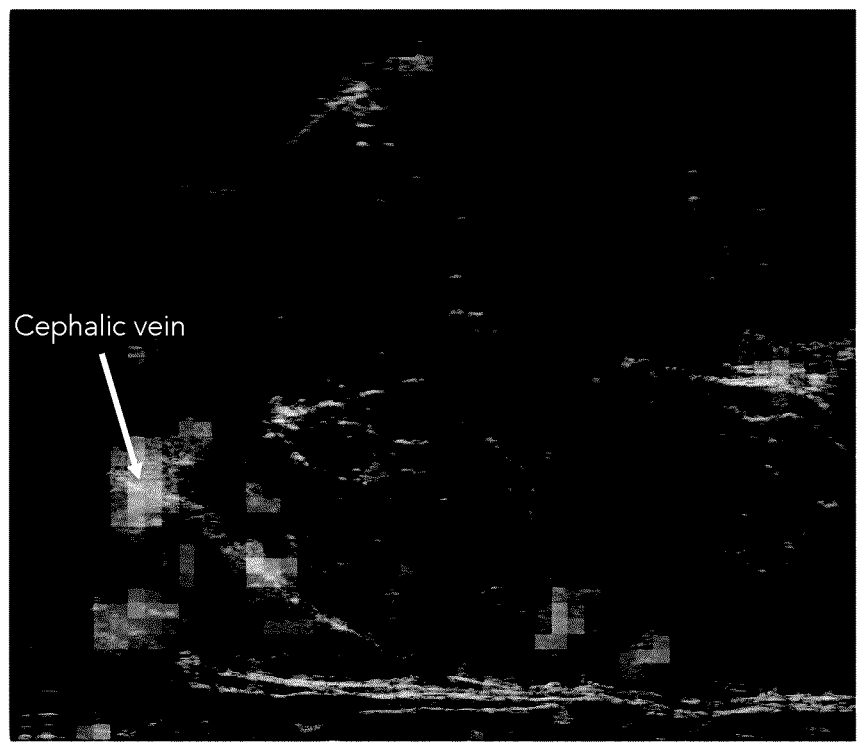
Figure 5C:
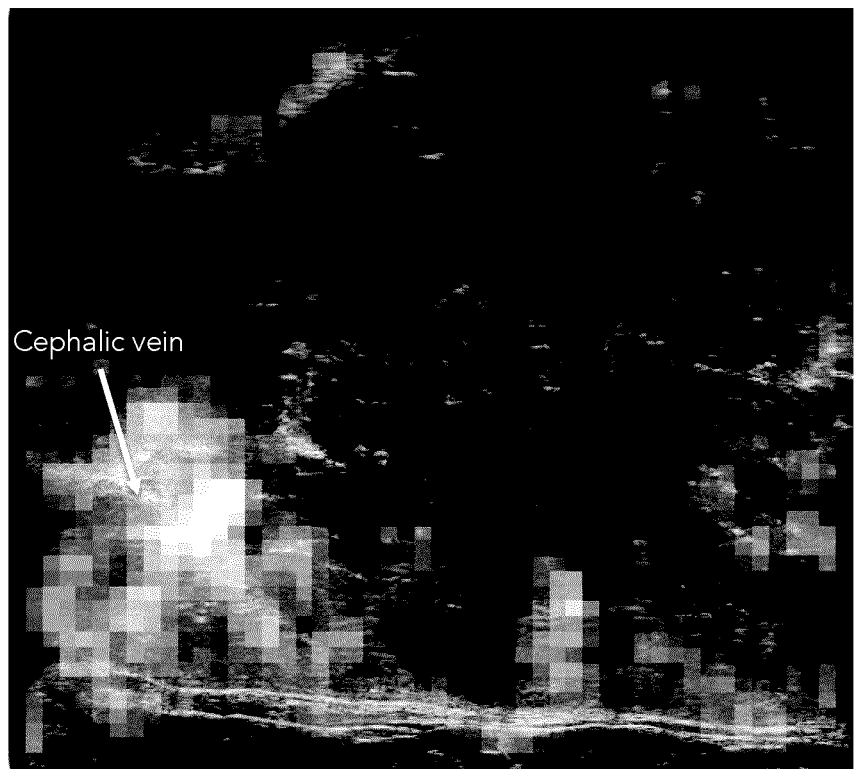

Increased blood flow in a tissue can occur during exercise and is also common in solid tumours and other cancerous growths. Exercise induced increased blood flow is shown in FIGS. 5A-C are before and after activation of a forearm muscle. FIG. 5A shows the anatomy of the wrist in a B mode micro-ultrasound image. FIG. 5B shows an image of the flexor digitorum at rest. FIG. 5C shows an image of the flexor digitorum at rest after being activated for 1 min.

Figure 6:
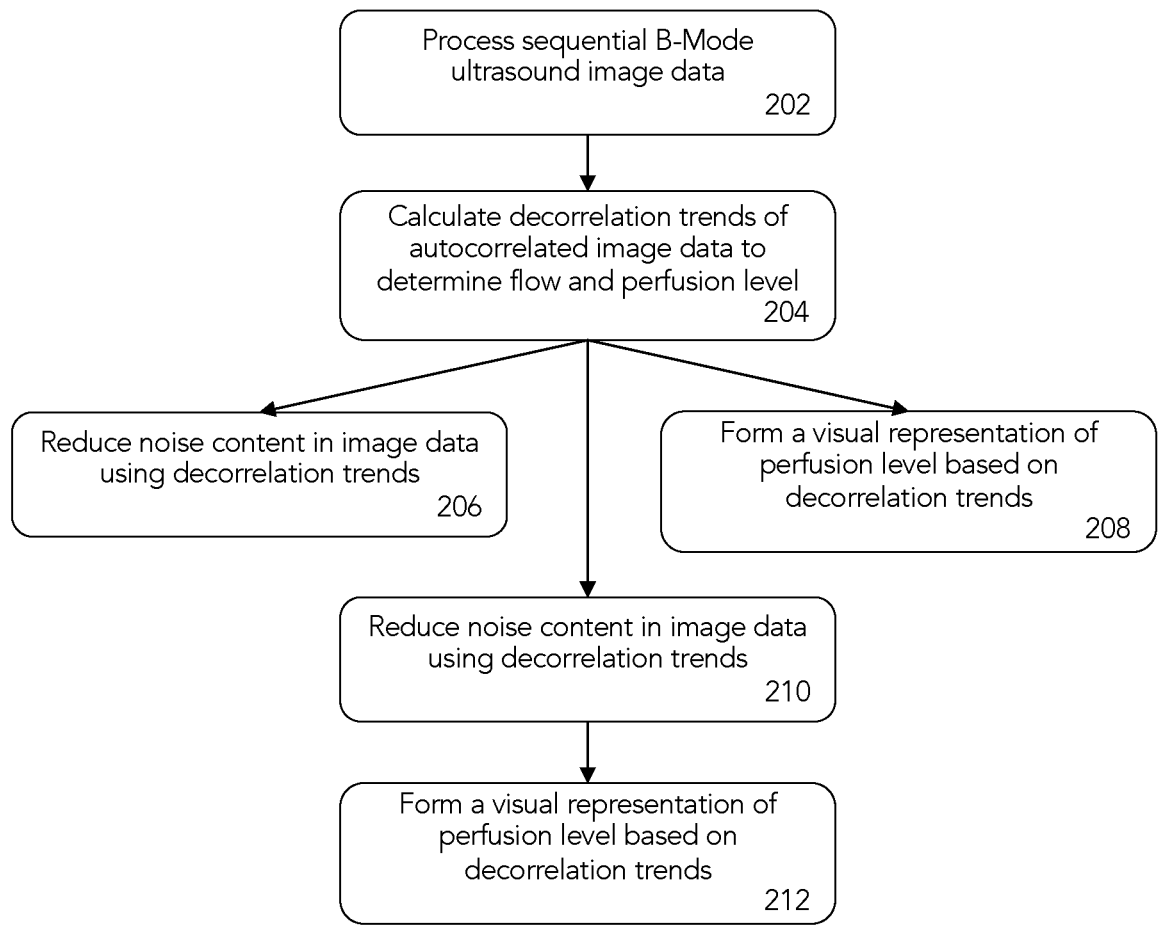
FIG. 6 is a flowchart illustrating an example method of ultrasound perfusion imaging.

FIG. 6 is a flowchart illustrating an example method of an ultrasound imaging mode for imaging perfusion in tissue. First, a plurality of B-Mode ultrasound image data is collected using high frequency ultrasound. In another embodiment, the plurality of B-Mode high frequency ultrasound image data (frames) are processed 202 from the memory 112. Then, decorrelation trends are calculated for the autocorrelated image data to determine flow and perfusion level 204 between selected image frames for each pixel in the image frames. Then, one of three steps may take place. In an embodiment, noise content in the image data is reduced by using the decorrelation trends 206. Or, a visual representation of the perfusion level is formed based on the decorrelation trends 208. Or, noise content in the image data is reduced by using the decorrelation trends, and a visual representation of the perfusion level is formed based on the decorrelation trends (shown as 210 and 212). Step 210 is the same as 206, and step 212 is the same as 208. Steps 210 and 212 may happen in any order. Also, the image data may be standardized at each pixel overall all images before auto-correlation (not shown).

The following clauses are offered as further description of the examples of the apparatus. Any one or more of the following clauses may be combinable with any another one or more of the following clauses and/or with any subsection or a portion or portions of any other clause and/or combination and permutation of clauses. Any one of the following clauses may stand on its own merit without having to be combined with any other clause or with any portion of any other clause.

Clause 1: An imaging processing method comprising: processing a plurality of digital images comprising sequential B-Mode ultrasound reflectivity data; calculating decorrelation trends of autocorrelated data to determine flow and perfusion level. Clause 2: A method of any of the clauses, or any portion of any clause, mentioned in this paragraph, further comprising: reducing noise content in the ultrasound data using the decorrelation trends. Clause 3: A method of any of the clauses, or any portion of any clause, mentioned in this paragraph, further comprising: forming a visual representation of the perfusion level based on the decorrelation trends. Clause 4: A method of any of the clauses, or any portion of any clause, mentioned in this paragraph, further comprising: reducing noise content in the autocorrelated data using the decorrelation trends; and forming a visual representation of the perfusion level based on the decorrelation trends. Clause 5: A method of any of the clauses, or any portion of any clause, mentioned in this paragraph, wherein the method has an image capture rate of 20 frames/sec or higher. Clause 6: A method of any of the clauses, or any portion of any clause, mentioned in this paragraph, wherein the image data is standardized before autocorrelation. Clause 7: A method of any of the clauses, or any portion of any clause, mentioned in this paragraph, wherein the autocorrelated data is normalized. Clause 8: A method of any of the clauses, or any portion of any clause, mentioned in this paragraph, wherein the decorrelation trend of the autocorrelated data is determined by linear regression, average difference, or overall magnitude change. Clause 9: A method of any of the clauses, or any portion of any clause, mentioned in this paragraph, wherein the autocorrelated data with non-linear trends are processed to determine one or more of period, exponential decay rate, time to local minima, or another measure of decorrelation. Clause 10: A method of any of the clauses, or any portion of any clause, mentioned in this paragraph, wherein the autocorrelation is calculated using a Spearman correlation, Pearson correlation, or Fourier Transform. Clause 11: A method of any of the clauses, or any portion of any clause, mentioned in this paragraph, further comprising a smoothing step prior to visual representation of the signal. Clause 12: A method of any of the clauses, or any portion of any clause, mentioned in this paragraph, further comprising application of thresholds and rescaling to the decorrelation trends before visual representation. Clause 13: A method of any of the clauses, or any portion of any clause, mentioned in this paragraph, further comprising a logarithmic transformation of the decorrelation trend. Clause 14: A method of any of the clauses, or any portion of any clause, mentioned in this paragraph, wherein the decorrelation trends are mapped to different colour or grayscale values for representation in an image. Clause 15: A method of any of the clauses, or any portion of any clause, mentioned in this paragraph, further comprising alignment of the plurality of digital images to correct for movement by matching local signal patterns between frames. Clause 16: A method of any of the clauses, or any portion of any clause, mentioned in this paragraph, wherein the method includes at least 5 frames of sequential B-Mode ultrasound reflectivity data Clause 17: A method of any of the clauses, or any portion of any clause, mentioned in this paragraph, wherein a subset of the image field is processed from each image to decrease processing time. Clause 18: A method of any of the clauses, or any portion of any clause, mentioned in this paragraph, wherein the image is downsampled to a lower resolution to decrease processing time. Clause 19: A method of any of the clauses, or any portion of any clause, mentioned in this paragraph, where in the ultrasound data is high frequency ultrasound with a frequency range greater than 15 MegaHertz. Clause 20: A perfusion imaging system comprising: a high frequency ultrasound transducer for capturing collecting a plurality of digital images comprising sequential B-Mode ultrasound reflectivity data; a signal processing unit, operatively connected to the transducer, the signal processing unit configured to calculate decorrelation trends of autocorrelated data to determine flow and perfusion level. Clause 21: A system of any of the clauses, or any portion of any clause, mentioned in this paragraph, wherein, the signal processing unit is further configured to reduce noise content in the ultrasound data using the decorrelation trends. Clause 22: A system of any of the clauses, or any portion of any clause, mentioned in this paragraph, wherein the signal processing unit is further configured to form a visual representation of the perfusion level based on the decorrelations trends. Clause 23: A system of any of the clauses, or any portion of any clause, mentioned in this paragraph, wherein the signal processing unit is further configured to reduce noise content in the ultrasound data using the decorrelation trends, and form a visual representation of the perfusion level based on the decorrelations trends. Clause 24: A system of any of the clauses, or any portion of any clause, mentioned in this paragraph, wherein the system has an image capture rate of 20 frames/sec or higher Clause 25: A system of any of the clauses, or any portion of any clause, mentioned in this paragraph, wherein the signal processing unit is configured to standardize the image data before autocorrelation. Clause 26: A computer readable storage medium, comprising executable instructions that when executed by a process cause the processor to: process a plurality of digital images comprising sequential B-Mode ultrasound reflectivity data obtained using a micro-ultrasound; calculate decorrelation trends of autocorrelated data to determine flow and perfusion level, Clause 27: A computer readable storage medium of any of the clauses or any portion of any clause, mentioned in this paragraph, further comprising instructions to: reduce noise content in the ultrasound data using the decorrelation trends. Clause 28: A computer readable storage medium of any of the clauses or any portion of any clause, mentioned in this paragraph, further comprising instructions to: form a visual representation of the perfusion level based on the decorrelation trends. Clause 29: A computer readable storage medium of any of the clauses or any portion of any clause, mentioned in this paragraph, further comprising instructions to: reduce noise content in the ultrasound data using the decorrelation trends; and form a visual representation of the perfusion level based on the decorrelation trends.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

What is claimed is:

1. An imaging processing method comprising:
   processing a plurality of digital images comprising sequential B-Mode ultrasound reflectivity data;
   calculating decorrelation trends of autocorrelated data to determine a perfusion level, including fluid flow, through tissue;
   reducing noise content in the autocorrelated data using the decorrelation trends; and
   forming a visual representation of the perfusion level based on the decorrelation trends.

2. The method claim 1, wherein the plurality of digital images are captured at a capture rate of 20 frames/sec or higher.

3. The method of claim 2, wherein the autocorrelation is calculated using a Spearman correlation, Pearson correlation, or Fourier Transform.

4. The method of claim 3, wherein image data for the plurality of digital images is standardized before autocorrelation.

5. The method of claim 4, wherein the autocorrelated data is normalized.

6. The method of claim 5, wherein the decorrelation trend of the autocorrelated data is determined by linear regression, average difference, or overall magnitude change.

7. The method of claim 6, wherein the autocorrelated data with non-linear trends are processed to determine one or more of period, exponential decay rate, time to local minima, or another measure of decorrelation.

8. The method of claim 7, wherein the method includes at least 5 frames of sequential B-Mode ultrasound reflectivity data.

9. The method of claim 8, further comprising alignment of the plurality of digital images to correct for movement by matching local signal patterns between frames.

10. The method of claim 9, wherein a patch is processed from each image to decrease processing time.

11. The method of claim 10, further comprising application of thresholds and rescaling to the decorrelation trends before visual representation.

12. The method of claim 11, further comprising a logarithmic transformation of the decorrelation trend.

13. The method of claim 12, wherein the decorrelation trends are mapped to different colour or grayscale values for representation in an image.

14. The method of claim 13, wherein each digital image of the plurality of digital images is downsampled to a lower resolution to decrease processing time.

15. The method of claim 14, where in the ultrasound data is high frequency ultrasound with a frequency range greater than 15 MegaHertz.

16. A perfusion imaging system comprising:
a high frequency ultrasound transducer for collecting a plurality of digital images comprising sequential B-Mode ultrasound reflectivity data;
a signal processing unit, operatively connected to the transducer, the signal processing unit configured to calculate decorrelation trends of autocorrelated data to determine a perfusion level, including fluid flow, through tissue;
reducing noise content in the autocorrelated data using the decorrelation trends; and
forming a visual representation of the perfusion level based on the decorrelation trends.

17. A non-transitory computer readable storage medium, comprising executable instructions that when executed by a processor cause the processor to:
process a plurality of digital images comprising sequential B-Mode ultrasound reflectivity data obtained using a micro-ultrasound;
calculate decorrelation trends of autocorrelated data to determine a perfusion level, including fluid flow, through tissue;
reduce noise content in the ultrasound data using the decorrelation trends; and
form a visual representation of the perfusion level based on the decorrelation trends.

* * * * *